United States Patent [19]
Baker

[11] 3,973,012
[45] Aug. 3, 1976

[54] ORGANOTIN MITICIDAL AND INSECTICIDAL METHOD

[75] Inventor: Don R. Baker, Orinda, Calif.

[73] Assignee: Stauffer Chemical Company, Westport, Conn.

[22] Filed: July 30, 1975

[21] Appl. No.: 600,340

Related U.S. Application Data

[62] Division of Ser. No. 466,930, May 6, 1974, Pat. No. 3,917,827, which is a division of Ser. No. 304,871, Oct. 19, 1972, Pat. No. 3,832,370.

[52] U.S. Cl. .................................. 424/203
[51] Int. Cl.² ................................. A01N 9/36
[58] Field of Search ..................... 424/200, 203

[56] References Cited
UNITED STATES PATENTS

| | | | |
|---|---|---|---|
| 2,725,333 | 11/1955 | Buntin ............................... | 424/203 |
| 3,634,479 | 1/1972 | Ridenour et al. ................ | 424/203 X |

Primary Examiner—Dale R. Ore
Attorney, Agent, or Firm—Daniel C. Block

[57] ABSTRACT

A composition of matter is described herein which has insecticidal and miticidal activity and methods of use. The composition may be defined by the following generic formula

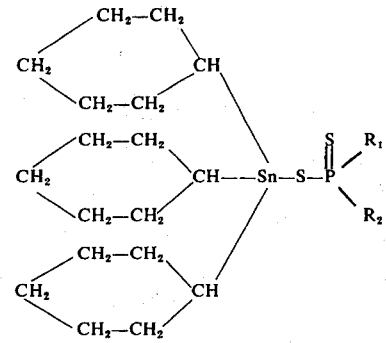

wherein $R_1$ is lower alkyl having 1 to 4 carbon atoms, and $R_2$ can be selected from alkylketoximino, piperidyl, cycloalkylketoximino, alkylaldoximino, alkylcarbamylalkoxy, hexamethyleneimino, alkyloxazolidine, and

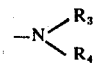

wherein $R_3$ and $R_4$ can be the same or different and can be selected from hydrogen, alkyl having 1 to 15 carbon atoms, alkoxyalkyl, alkenyl, benzyl, cyanoalkyl, alkanol, phenyl, alkylphenyl, sulfonamidophenyl, thiazolinyl, alkoxycarbamyl, halobenzyl, furfuryl, provided that when $R_3$ is hydrogen, $R_4$ is other than hydrogen.

1 Claim, No Drawings

ORGANOTIN MITICIDAL AND INSECTICIDAL METHOD

This is a division of application Ser. No. 466,930 filed on May 6, 1974, now U.S. Pat. No. 3,917,827, which is a divisional application of application Ser. No. 304,871, filed Oct. 19, 1972, now U.S. Pat. No. 3,832,370.

BACKGROUND OF THE INVENTION

Among the many insecticidal and miticidal compounds available, the organotin compounds have reached a relatively high degree of commercial success. Specifically, the organotins described in U.S. Pat. Nos. 3,264,177, 3,591,614 and 3,591,615 are widely used. These compounds, however, suffer from considerable unstability due to the presence of an ester linkage to the tin atom. Thus, these compounds are quite susceptible to hydrolysis on use. Additionally, the organotin compounds described in U.S. Pat. Nos. 3,321,361 and 3,321,365 are useful as insecticides. However, these compounds are quite toxic to vegetation and thus have extremely limited use.

BRIEF DESCRIPTION OF THE INVENTION

It has been discovered that certain organotin compounds have relatively low phytotoxicity properties and are relatively stable. These organotin compounds may be defined by the following generic formula

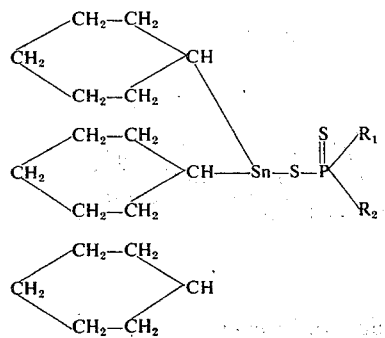

wherein $R_1$ is lower alkyl having 1 to 4 carbon atoms, and $R_2$ can be selected from alkylketoximino, piperidyl, cycloalkylketoximino, alkylaldoximino, alkylcarbamylalkoxy, hexamethyleneimino, alkyloxazolidine, and

wherein $R_3$ and $R_4$ can be the same or different and can be selected from hydrogen, alkyl having 1 to 15 carbon atoms, alkoxyalkyl, alkenyl, benzyl, cyanoalkyl, alkanol, phenyl, alkylphenyl, sulfonamidophenyl, thiazolinyl, alkoxycarbamyl, halobenzyl, furfuryl, provided that when $R_3$ is hydrogen, $R_4$ is other than hydrogen.

DETAILED DESCRIPTION OF THE INVENTION

In the practice of the present invention, the compounds of the present invention are manufactured by reacting an alkylthiophosphine sulfide with an appropriate amine in a neutral solvent to form an intermediate compound. The intermediate compound is then reacted with an alkyl tin halide to form the end product. The halide moiety in the alkyl tin halide can be selected from the group consisting of chlorine, bromine and iodine. After the compounds of the present invention are formed, they can be applied to the habitat in an effective amount to control respective mites and insects.

The following examples illustrate the merits of the present invention:

EXAMPLE 1

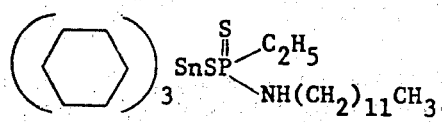

A mixture was formed containing 2.2 grams (0.009 mole) of ethylthiophosphine sulfide, 50 ml. of tetrahydrofuran, 2.8 grams (0.015 mole) of dodecylamine and 7.0 ml. of triethylamine. This mixture was allowed to stand for 1 hour wherein 6.1 grams (0.015 mole) of tricyclohexyl tin chloride was added and the mixture was allowed to stand for 24 hours. Then, the mixture was heated to boiling for a few minutes, then diluted with 100 ml. of chloroform, washed with 100 ml. of water and 50 ml. of sodium bicarbonate solution, dried over magnesium sulfate and evaporated in vacuo to yield 6.5 grams of product.

EXAMPLE 2

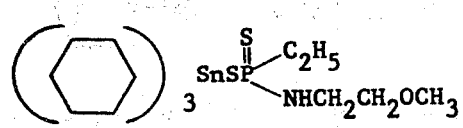

A mixture was formed containing 2.2 grams (0.009 mole) of ethylthiophosphine sulfide, 50 ml. tetrahydrofuran, and 3.0 grams (0.04 mole) of methoxyethylamine. The mixture was allowed to stand for 1 hour, wherein 6.1 grams (0.015 mole) of tricyclohexyl tin chloride was added. The mixture was allowed to stand for 24 hours. Then, the mixture was heated to boiling for a few minutes, diluted with 100 ml. of chloroform, washed with 100 ml. of water and a 50 ml. solution of sodium bicarbonate, dried over magnesium sulfate and evaporated in vacuo to yield 6.5 grams of product, m.p. 56°–59°C.

EXAMPLE 3

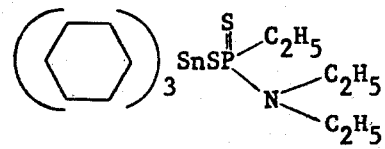

A mixture was formed containing 2.2 grams (0.009 mole) of ethylthiophosphine sulfide, 50 ml. of ethyl ether and 4.1 ml. (0.04 mole) of diethylamine. This mixture was allowed to stand for 1 hour. Then, 6.1 grams (0.015 mole) of tricyclohexyl tin chloride and 50 ml. tetrahydrofuran was added and the mixture was allowed to stand for 24 hours. Then, the mixture was boiled for a few minutes, diluted with 50 ml. of ethyl ether and then washed with 100 ml. of water, 50 ml. of a saturated solution of sodium bicarbonate, dried over magnesium sulfate and evaporated in vacuo to yield 7.0 grams of product.

EXAMPLE 4

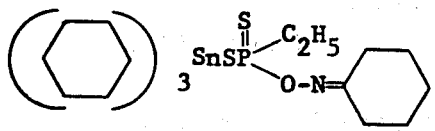

A mixture was formed containing 2.2 grams (0.009 mole) of ethylthiophosphine sulfide, 50 ml. tetrahydrofuran, 1.70 grams (0.015 mole) of cyclohexanoneoxime and 7.0 ml. of triethylamine. This mixture reacted exothermically with the addition of triethylamine. After 1 hour, 6.0 grams (0.015 mole) of tricyclohexyl tin chloride was added and allowed to stand for 2 days. The mixture was diluted with 100 ml. of chloroform. The mixture was then washed with 100 ml. of water, 50 ml. of saturated sodium bicarbonate solution, dried over magnesium sulfate and evaporated in vacuo to yield an oil that was triturated with methanol to yield 7.2 g. of crystals, m.p. 76°–79°C.

EXAMPLE 5

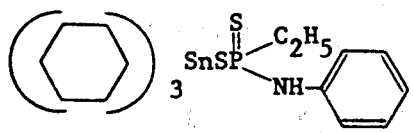

The procedure of Example 4 was repeated in its entirety except 1.8 grams (0.019 mole) of aniline was substituted for the 1.70 grams of cyclohexanoneoxime. The yield was 6.0 grams of product, m.p. 88°–90°C.

EXAMPLE 6

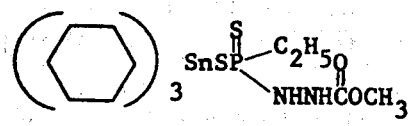

The procedure of Example 4 was repeated in its entirety except 1.37 grams (0.015 mole) of methylhydrazinocarboxylate was substituted for the 1.70 grams of cyclohexanoneoxime and only a 24 hour reaction period was used instead of 2 days. The yield was 5.0 grams of product, m.p. 83°–86°C.

EXAMPLE 7

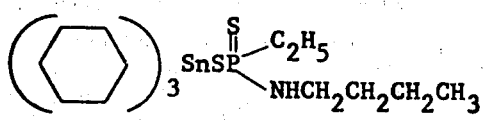

A mixture was formed containing 2.2 grams (0.009 mole) of ethylthiophosphine sulfide, 50 ml. tetrahydrofuran, 2.0 ml. (0.02 mole) n-butylamine, and 7.0 ml. of triethylamine. After standing at room temperature for 1 hour, 5.0 grams (0.0124 mole) of tricyclohexyl tin chloride was added in one portion and the mixture was allowed to stand until the next morning. The mixture was diluted with 100 ml. of chloroform and then washed with 100 ml. of water, 50 ml. of 1N HCl, 50 ml. of saturated sodium bicarbonate solution and then dried over magnesium sulfate and evaporated in vacuo to give an oil that was crystallized from 50 ml. of methyl alcohol to yield 6.0 grams of product, m.p. 58°–60°C.

EXAMPLE 8

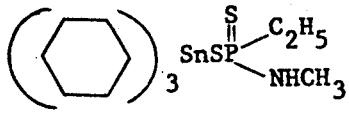

The procedure of Example 7 was repeated in its entirety except 1.1 grams of methylamine gas was substituted for the n-butylamine. The product yield was 3.8 grams, m.p. 81°–83°C.

Other compounds were made in a similar manner using appropriate starting materials. The compounds are listed in Table I.

TABLE I

| Example 9 | 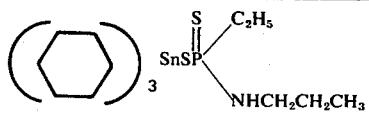 |
| --- | --- |
| Example 10 | 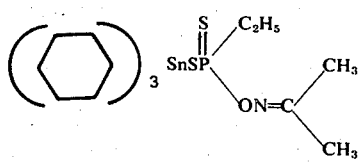 |
| Example 11 | 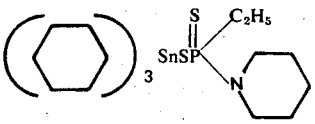 |

TABLE I-continued
Example 12 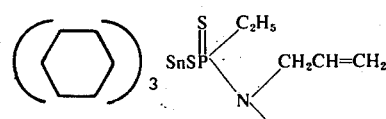
Example 13 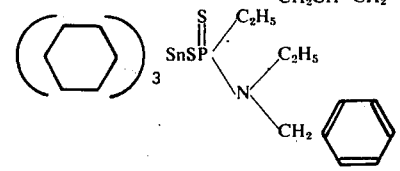
Example 14 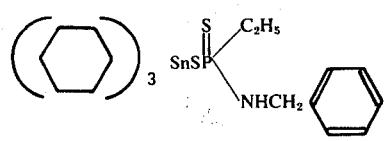
Example 15 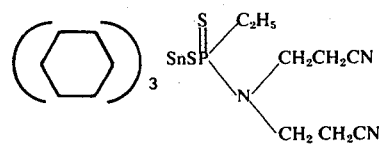
Example 16 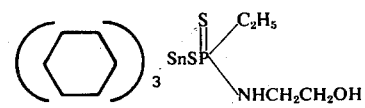
Example 17 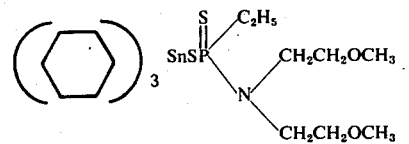
Example 18 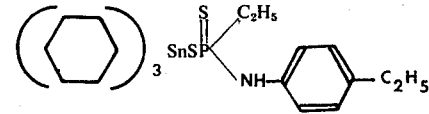
Example 19 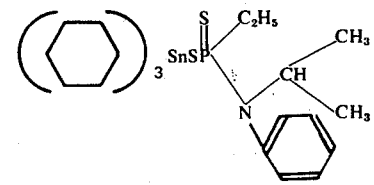
Example 20 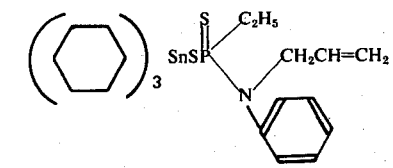
Example 21 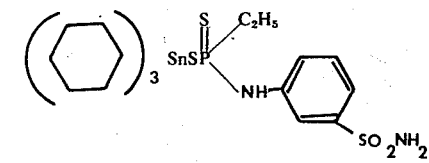

TABLE I-continued
Example 22 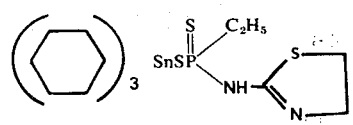
Example 23 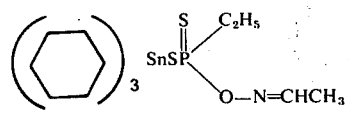
Example 24 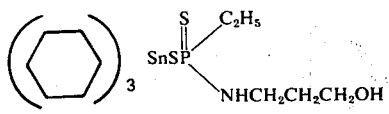
Example 25 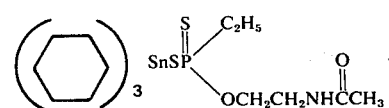
Example 26 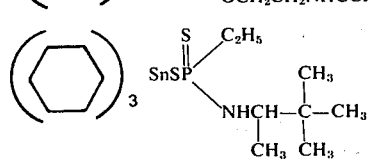
Example 27 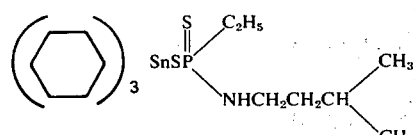
Example 28 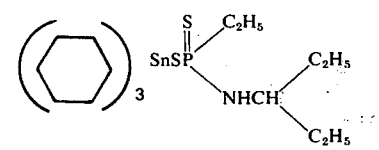
Example 29 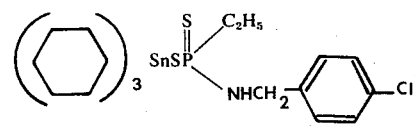
Example 30 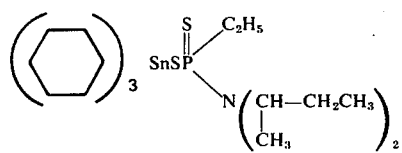
Example 31 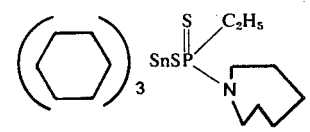
Example 32 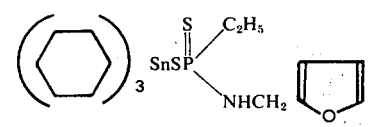

TABLE I-continued

Example 33 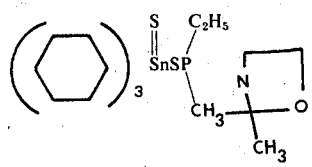

Example 34 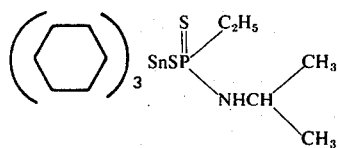

Example 35 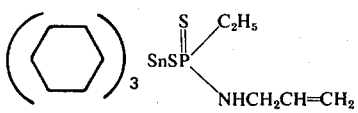

Insecticidal Evaluation Tests

The following insect species are subjected to evaluation tests for insecticidal activity.
1. Housefly (HF) - Musca domestica (Linn.)
2. Lygus Bug (LB) - Lygus hesperus (Knight)
3. Bean Aphid (BA) - Aphis fabae (Scop.)
4. Two-spotted Mite (2-SM) - Tetranychus urticae (Koch)
5. Salt-Marsh Caterpillar (SMC) - Estigmene acrea (Drury)
6. Beet armyworm (BAW) - Spodoptera exigua (Hubner)
7. Tobacco budworm (TBW) - Heliothis virescens (Fabricius)

Aliquots of the toxicants, dissolved in an appropriate solvent, are diluted in water containing 0.018% of a wetting agent, Sponto 221 (a polyoxyether of alkylated phenols blended with organic sulfonates). Test concentrations range from 0.1% downward to that at which 50% mortality is obtained. In the tests, for these species, ten 1-month old nymphs of the Lygus Bug are placed in a circular cardboard cage sealed on one end with cellophane and covered by a cloth netting on the other. Test concentrations for the Lygus Bug ranged from 0.05% downward to that at which 50% mortality was obtained. Each of the aqueous suspensions of the candidate compounds are sprayed onto the insects through the cloth netting by means of a hand spray gun. Percent mortality in each case is recorded after 72 hours, and the $LD_{50}$ value expressed as percent of toxicant in the aqueous spray is recorded. The results are in Table II under Column LB.

The following procedure is used to test houseflies: A stock solution containing 0.1 percent by weight of the toxicant in an appropriate solvent is prepared. Aliquots of this solution are combined with 1 milliliter of an acetone-peanut oil solution in a 60 mm O.D. aluminum pan and allowed to dry. The aliquots are selected to achieve desired toxicant concentration ranging from 100 μg per aluminum pan to that at which 50% mortality was attained. The aluminum pans are placed in a circular cardboard cage, closed on the bottom with cellophane and covered on top with cloth netting. Twenty-five female houseflies are introduced into the cage and the percent mortality is recorded after 48 hours. The $LD_{50}$ values are expressed in terms of μg per 25 female flies. $LD_{50}$ values obtained in the above-mentioned housefly test are found in Table II under Column HF.

The compound is dissolved in the appropriate solvent and diluted to a concentration of 0.1 percent with water containing 0.018% Sponto 221. A portion of the leaf from a bitter dock (Rumex obtusifolius) plant is immersed in the test solution for 10 seconds are allowed to dry. When dry, the leaf is placed in a Petri dish containing a 9 cm disc of moistened filter paper. Five 3rd-instar saltmarsh caterpillar larvae are placed on the treated leaf. Mortality is recorded after 72 hours. Test concentrations range from 0.1 percent to that at which 50% mortality is obtained. This latter concentration is recorded as the $LD_{50}$ value for the test compound.

The test method for the cotton bollworm, beet armyworm and tobacco budworm is identical to the above except that Romaine lettuce (Lactuca sativa) is used as the test plant rather than bitter dock.

The compounds are also active against two-spotted mite (2-SM) Tetranychus urticae (Koch). Pinto bean plants (Phaseolus sp.) are utilized as the host plant and infested with 50 to 75 mites of various ages. Twenty-four hours after infestation, they are sprayed to the point of run off with aqueous suspension of the toxicant. Test concentrations range from 0.05% to that at which 50% mortality is obtained. The values obtained in this test are found in Table II under the Columns 2SM-PE and 2SM-Eggs.

The compounds are also active against bean aphid (Aphis fabae (Scop.)) as a contact toxicant. The same test procedure as given for the two-spotted mite above is used for the bean aphid except nasturtium (Tropaeolum Sp.) plants approximately 2 to 3 inches tall are used as the host plant. The $LD_{50}$ values obtained for the compounds of this invention are found in Table II under Column BA.

TABLE II

| Example No. | HF | LB | BA | PE | Eggs | 2-SM SMC | BAW | TBW |
|---|---|---|---|---|---|---|---|---|
| 1 | 80 | >.05 | 0.01 | .0003 | .0008 | .03 | .03 | .1 |
| 2 | 50 | >.05 | >.05 | .0003 | .0008 | .01 | .01 | .1 |
| 3 | 75 | >.05 | .01 | .0001 | .003 | .03 | .01 | >.1 |
| 4 | 65 | >.05 | .003 | .0003 | .003 | >.1 | .03 | >.1 |
| 5 | 65 | >.05 | .008 | .003 | .003 | >.1 | .01 | >.1 |
| 6 | 65 | >.05 | .03 | .0003 | .003 | .1 | .08 | >.1 |
| 7 | 65 | >.05 | .03 | .0003 | .0008 | .03 | .008 | .1 |
| 8 | 65 | >.05 | .03 | .0003 | .0008 | .05 | .008 | >.1 |
| 9 | 40 | .05 | .05 | .0003 | .003 | — | — | >.1 |
| 10 | 50 | .05 | .03 | .0001 | .003 | — | — | >.1 |
| 11 | 80 | .02 | .03 | .0003 | .003 | — | — | >.1 |
| 12 | 55 | .05 | .01 | .0005 | .003 | .01 | .03 | .1 |
| 13 | 60 | .05 | .01 | .0003 | .003 | .1 | .03 | >.1 |
| 14 | 80 | .05 | .01 | .0003 | .0008 | .1 | .01 | >.1 |
| 15 | 80 | >.05 | .05 | .0003 | .003 | .05 | .01 | >.1 |
| 16 | >100 | >.05 | >.05 | .003 | .03 | >.1 | — | — |
| 17 | 80 | .05 | .03 | .0003 | .0008 | >.1 | .01 | >.1 |
| 18 | 90 | .05 | .03 | .001 | .008 | >.1 | .01 | >.1 |
| 19 | 90 | .05 | .008 | .0005 | .008 | .1 | .01 | .1 |
| 20 | >100 | >.05 | .03 | .001 | .008 | >.1 | .01 | >.1 |
| 21 | 65 | >.05 | .01 | .0003 | .003 | .1 | .1 | >.1 |
| 22 | 65 | >.05 | .05 | .0003 | .003 | .1 | .1 | >.1 |
| 23 | 65 | >.05 | .03 | .0003 | .003 | >.1 | .05 | >.1 |
| 24 | 65 | >.05 | .01 | .0003 | .003 | .1 | .05 | >.1 |
| 25 | 65 | >.05 | .005 | .0003 | .003 | >.1 | .05 | >.1 |
| 26 | 65 | .05 | .008 | .0001 | .0008 | .05 | .005 | .08 |
| 27 | 65 | >.05 | .005 | .0003 | .003 | .05 | .01 | >.1 |
| 28 | 65 | >.05 | .03 | .0003 | .0008 | >.05 | .01 | >.1 |
| 29 | 65 | >.05 | .008 | .0005 | .0008 | .03 | .005 | >.1 |
| 30 | 65 | .05 | .008 | .0003 | .003 | .05 | .005 | >.1 |
| 31 | 80 | >.05 | .03 | .0003 | .0008 | .05 | .005 | >.1 |
| 32 | 65 | >.05 | .03 | .0003 | .0008 | >.1 | .005 | >.1 |
| 33 | 65 | >.05 | .03 | .0003 | .0008 | .1 | .005 | .08 |
| 34 | 65 | >.05 | .03 | .0003 | .0008 | >.1 | .01 | .05 |
| 35 | 65 | >.05 | .03 | .0001 | .003 | .1 | .005 | .1 |

The compounds of this invention are generally embodied into a form suitable for convenient application. For example, the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays; propellants, such as dichlorodifluoromethane, etc. If desired, however, the active compounds can be applied directly to feedstuffs, seeds, etc. upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise not more than about 50.0% by weight of the composition. Preferably, however, the pesticide compositions of this invention will be in the form of spray tank solutions or suspensions containing about 0.1 to 1.0% by weight of the active pesticide compound.

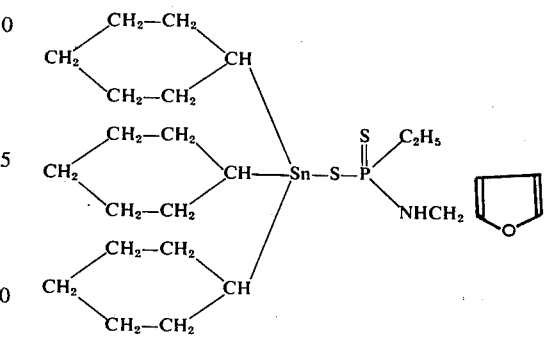

What is claimed is:

1. The method which comprises the step of killing insects and mites by contacting them with an amount lethal thereto of a compound of the formula: